United States Patent
Durham

(10) Patent No.: US 11,357,871 B2
(45) Date of Patent: Jun. 14, 2022

(54) CHALLENGE TEST FOR DIAGNOSING SUBTYPES OF ASD

(71) Applicant: Stalicla S.A., Geneva (CH)

(72) Inventor: Lynn Durham, Geneva (CH)

(73) Assignee: Stalicla S.A., Geneva (CH)

( * ) Notice: Subject to any disclaimer, the term of this patent is extended or adjusted under 35 U.S.C. 154(b) by 259 days.

(21) Appl. No.: 16/182,544

(22) Filed: Nov. 6, 2018

(65) Prior Publication Data

US 2019/0134230 A1    May 9, 2019

Related U.S. Application Data

(60) Provisional application No. 62/582,198, filed on Nov. 6, 2017.

(30) Foreign Application Priority Data

Nov. 6, 2017 (EP) .................................. 17200185

(51) Int. Cl.
| | |
|---|---|
| *A61P 25/00* | (2006.01) |
| *A61K 36/31* | (2006.01) |
| *A61K 49/00* | (2006.01) |
| *A61K 31/26* | (2006.01) |
| *A61K 31/196* | (2006.01) |
| *A61K 31/27* | (2006.01) |
| *A61K 31/366* | (2006.01) |
| *A61K 31/44* | (2006.01) |
| *A61K 38/45* | (2006.01) |
| *A61P 43/00* | (2006.01) |
| *A61K 31/555* | (2006.01) |
| *A61K 31/335* | (2006.01) |
| *A61K 31/05* | (2006.01) |
| *A61K 31/047* | (2006.01) |
| *A61K 31/11* | (2006.01) |
| *A61K 31/497* | (2006.01) |
| *A61K 31/225* | (2006.01) |
| *A61K 31/122* | (2006.01) |
| *A61K 38/06* | (2006.01) |
| *A61K 31/10* | (2006.01) |
| *A61K 31/155* | (2006.01) |
| *A61K 31/192* | (2006.01) |

(Continued)

(52) U.S. Cl.
CPC .......... *A61K 49/0004* (2013.01); *A61B 5/167* (2013.01); *A61K 31/047* (2013.01); *A61K 31/05* (2013.01); *A61K 31/10* (2013.01); *A61K 31/11* (2013.01); *A61K 31/122* (2013.01); *A61K 31/155* (2013.01); *A61K 31/192* (2013.01); *A61K 31/196* (2013.01); *A61K 31/203* (2013.01); *A61K 31/225* (2013.01); *A61K 31/26* (2013.01); *A61K 31/27* (2013.01); *A61K 31/335* (2013.01); *A61K 31/343* (2013.01); *A61K 31/352* (2013.01); *A61K 31/365* (2013.01); *A61K 31/366* (2013.01); *A61K 31/375* (2013.01); *A61K 31/44* (2013.01); *A61K 31/4409* (2013.01); *A61K 31/4425* (2013.01); *A61K 31/497* (2013.01); *A61K 31/555* (2013.01); *A61K 36/062* (2013.01); *A61K 36/31* (2013.01); *A61K 38/063* (2013.01); *A61K 38/1706* (2013.01); *A61K 38/1709* (2013.01); *A61K 38/45* (2013.01); *A61P 25/00* (2018.01); *A61P 43/00* (2018.01)

(58) Field of Classification Search
CPC ......... A61P 25/00; A61B 5/167; A61K 36/31; A61K 31/047; A61K 31/05; A61K 31/11; A61K 31/122; A61K 31/155; A61K 31/225; A61K 31/26; A61K 31/335; A61K 31/497; A61K 31/555; A61K 38/063
See application file for complete search history.

(56) References Cited

FOREIGN PATENT DOCUMENTS

| WO | WO-2010/062681 A2 | 6/2010 | |
|---|---|---|---|
| WO | WO 2013/067040 A1 | 5/2013 | |
| WO | WO-2016054475 A1 * | 4/2016 | ............. A23L 33/40 |

OTHER PUBLICATIONS

University of Massachusetts, Worcester ,"Sulforaphane Treatment of Children With Autism Spectrum Disorder (ASD)", NCT02561481, ClinicalTrials.gov, Sep. 28, 2015 (Year: 2015).*

(Continued)

*Primary Examiner* — Lianko G Garyu
(74) *Attorney, Agent, or Firm* — Millen, White, Zelano & Branigan, PC; Ryan Pool

(57) ABSTRACT

The present invention is directed to a method for differentiating between ASD phenotype 1, phenotype 2 and other ASD patients, wherein the method comprises: administering an Nrf2-activator to a subject, and identifying the subject as an ASD phenotype 1 patient if the subject shows a negative response, as a phenotype 2 patient if he shows a positive response and as another ASD patient if he does not show a positive nor a negative response, wherein the subject is a patient previously diagnosed with idiopathic ASD or a subject displaying clinical signs of ASD. Likewise, the present invention is directed to an Nrf2-activator for use in differentiating between autism spectrum disorder (ASD) phenotype 1 patients, phenotype 2 patients and other ASD patients, wherein the Nrf2-activator is administered to a subject, wherein a phenotype 1 patient is identified by a negative response, a phenotype 2 patient is identified by a positive response and other ASD patients are identified by the absence of a positive and a negative wherein the subject is a patient previously diagnosed with idiopathic ASD or a subject displaying clinical signs of ASD.

4 Claims, No Drawings

(51) Int. Cl.
| | |
|---|---|
| A61K 31/203 | (2006.01) |
| A61K 31/343 | (2006.01) |
| A61K 31/352 | (2006.01) |
| A61K 31/365 | (2006.01) |
| A61K 31/375 | (2006.01) |
| A61K 31/4409 | (2006.01) |
| A61K 31/4425 | (2006.01) |
| A61K 36/062 | (2006.01) |
| A61K 38/17 | (2006.01) |
| A61B 5/16 | (2006.01) |

(56) References Cited

OTHER PUBLICATIONS

Singh et al. "Sulforaphane treatment of autism spectrum disorder (ASD)", PNAS, 2014, pp. 15550-15555 (Year: 2014).*

Singh et al., "Sulforaphane treatment of autism spectrum disorder (ASD)", PNAS, 2014, 15550-15555 (Year: 2014).*

Singh et al, "Sulforaphane Treatment of Young Men with Autism Spectrum Disorder", CNS & Neurological Disorders—Drug Targets, 2016, 15, 597-601 (Year: 2016).*

Abrahams, et al., "Advances in autism genetics: on the threshold of a new neurobiology," Nat Rev Genet., vol. 9(6), p. 493 (Jun. 2008).

Zoghbi, et al., "Synaptic dysfunction in neurodevelopmental disorders associated with autism and intellectual disabilities," Cold Spring Harb. Perspect. Biol., vol. 1; 4(3), 22 pages (Mar. 2012).

Persico et al., "Searching for ways out of the autism maze: genetic, epigenetic and environmental clues," *Trends Neuroscience*, vol. 29(7):349-358 (Jul. 2006).

Folstein, et al., "Infantile autism: a genetic study of 21 twin pairs," *J Child Psychol. Psyquiatry*, Sep;18(4): 297-321 (1977).

Sandin, et al., "The Heritability of Autism Spectrum Disorder," JAMA, vol. 318(12), pp. 1182-1184 (2017).

Ronemus et al, "The role of the novo mutations in the genetics of autism spectrum disorders," Nat Rev Genet., vol. 15(2), pp. 133-141 (Feb. 2014).

Gilman, et al., "Rare de novo variants associated with autism implicate a large functional network of genes involved in information and function of synapses," Neuron., vol. 70(5), pp. 898-907 (Jun. 2011).

O'Roak et al., "Sporadic autism exomes reveal a highly interconnected protein network of de novo mutations," Nature, vol. 4, pp. 485(7397), pp. 246-250 (Apr. 2012).

De Rubeis, et al., "Synaptic, transcriptional and chromatin genes disrupted in autism," Nature., 13; 515 (7526), pp. 209-215 (Nov. 2014).

Myka, et al., "Immune mediators in the brain and peripheral tissues in autism spectrum disorder," *Nature Reviews Neuroscience* 16, 469-486 (2015).

Subramanian, "Characterizing Autism Spectrum Disorders by Key Biochemical Pathways," *Frontiers in Neuroscience*, vol. 9, No. 313, pp. 1131-1143 (Sep. 2015).

Bernier et al., "Disruptive CHD8 mutations define a subtype of autism early in development," Cell; 158 (2): 263-276 (Jul. 2014).

Eapen, et al., "Autism Spectrum Disorders: From genotypes to phenotypes," Front Hum Neurosci., 8:914 (2014).

Bochner et al., "Assay of the multiple energy-producing pathways of mammalian cells," PLoS One, 6(3):e18147 (2011).

Dreger et al., Nrf2-dependent upregulation of antioxidative enzymes: a novel pathway for proteasome inhibitor-mediated cardioprotection. *Cardiovasc Research*, 83(2): p. 354-61 (2009).

Higgins et al., Transcription factor Nrf2 mediates an adaptive response to sulforaphane that protects fibroblasts in vitro against the cytotoxic effects of electrophiles, peroxides and redox-cycling agents. *Toxicol Appl Pharmacol*, 2009. 237(3): p. 267-80 (2009).

Shin et al., "Role of the Nrf2-ARE pathway in liver diseases,". *Oxid Med Cell Longev*, p. 763257 (2013).

Tang, et al., "Loss of mTOR-dependent macroautophagy causes autistic-like synaptic pruning deficits," *Neuron*, 83(5), pp. 1131-1143 (2014).

Singh, et al., Sulforaphane Treatment of Autism Spectrum Disorder (ASD), *PNAS* 111(43), pp. 15550-15555 (Oct. 2014).

Coleta et al., "Assessment of Luteolin (3',4',5,7-Tetrahydroxyflavone) Neuropharmacological Activity", *Behavioral Brain Research*, vol. 189, pp. 75-82 (2008).

Non-Final Office Action on U.S. Appl. No. 16/182,546 dated Dec. 27, 2019.

Song et al., "Autonomic Dysfunction and Autism: Subtypes and Clinical Perspectives", *North American Journal of Medicine and Science*, vol. 9, No. 4, pp. 172-180 (Oct. 2016).

* cited by examiner

CHALLENGE TEST FOR DIAGNOSING SUBTYPES OF ASD

CROSS-REFERENCE TO RELATED APPLICATIONS

This application claims priority from U.S. Provisional Patent Application No. 62/582,198, filed Nov. 6, 2017, and European Patent Application No. 17200185.1, filed Nov. 6, 2017. The contents of these applications are incorporated herein by reference in their entirety.

FIELD OF THE INVENTION

The invention relates to a method of differentiating between subtypes of idiopathic autism spectrum disorder (ASD), in particular of classifying and identifying subgroups of ASD patients such as phenotype 1 and phenotype 2 which are characterized by specific molecular and/or genetic underlying alterations.

BACKGROUND OF THE INVENTION

Autism spectrum disorder (ASD) are a group of neurodevelopmental disorder frequently characterized by impairments in social interactions, difficulties with language and communication, and the presence of repetitive, perseverative behaviors (Abrahams B S, Geschwind D H; Advances in autism genetics: on the threshold of a new neurobiology; Nat Rev Genet. 2008 June; 9(6):493), (Zoghbi H Y, Bear M F; Synaptic dysfunction in neurodevelopmental disorders associated with autism and intellectual disabilities; Cold Spring Harb Perspect Biol. 2012 Mar. 1; 4(3)). Characteristic symptoms or behavioral traits of ASD typically appear during the first three years of life and remain present throughout life in the vast majority of patients. Intensity of symptoms may vary from patient to patient and may decrease as the patient develops adaptive skills. Environmental factors, developmental or comorbidities such as epilepsy can also result in a worsening of symptoms. According to the fifth edition of the diagnostic and statistical manual of mental disorders (DSM. 5th Edition. Washington, D.C.: American Psychiatric Association; 2013. American Psychiatric Association. Diagnostic and Statistical Manual of Mental Disorders), ASD is characterized by two sets of core impairments: persisting deficits of social communication and interaction; restricted and repetitive behaviors, interests, activities. Compared to the previous edition (DSM-IV-Text Revision) (DSM-IV-TR 4th Edition. Washington, D.C.: American Psychiatric Association; 2000. American Psychiatric Association. Diagnostic and Statistical Manual of Mental Disorders.) DSM-5 introduced significant changes. In the diagnostic criteria, language abilities not employed in social communication have been de-emphasized. Further, the diagnostic subcategories, namely autistic disorder, Asperger disorder, Rett disorder, childhood disintegrative disorder, and pervasive developmental disorder (PDD) not otherwise specified are now encompassed by the diagnostic criteria for autism spectrum disorder. DSM-5 additionally requires to specify where patient fits within three levels of increasing severity of ASD, from (1) ("requiring support") to (2) ("requiring substantial support"), up to (3) ("requiring very substantial support"). Other related behaviorally based definitions for Autism are proposed under various terminologies in other diagnostic manuals and classification system including the WHO-ICD-10 definition of Autistic Disorder (2017/18 ICD-10-CM Diagnosis Code F84.0) (World Health Organization. (1992). The ICD-10 classification of mental and behavioural disorders: clinical descriptions and diagnostic guidelines (Geneva: World Health Organization). While ASD can be defined by symptoms in core areas, there exists significant heterogeneity in genetics, phenotypes, clinical presentation, and associated comorbidities (Persico A M, Bourgeron T; Searching for ways out of the autism maze: genetic, epigenetic and environmental clues; Trends Neurosci. 2006 July; 29(7):349-358). The genetic contribution to the causation/predisposition to autism is considered to be substantial on the basis of high concordance in monozygous twins (Folstein S. Rutter M; Infantile autism: a genetic study of 21 twin pairs; J Child Psychol Psyquiatry; 1977 September; 18(4): 297-321.). A recently published reanalysis of data from a previous study on the familial risk for autism spectrum disorder (ASD) further supports these initial findings suggesting that genetics contributes 83% of the risk for ASD. Environmental factors thus seem to play a minor 17% though significant role in the developmental etiology of ASD. (Sandin 5, Lichtenstein P, Kuja-Halkola R, Hultman C, Larsson H, Reichenberg A. The Heritability of Autism Spectrum Disorder. JAMA. 2017; 318(12):1182-1184. doi:10.1001/jama.2017.12141.) However, to further complexity matters genetic and epigenetic factors intertwine with prenatal and lifelong dynamic environmental factors to draw individual patient pathogenesis. There is growing perception among the scientific community that the current behavioral based approaches to diagnostic do not allow for efficient classification of patients in terms of molecular and genetic alterations, but rather serve as a behavioral umbrella term for a large group of neurodevelopmental disorders with different etiologies. Recent developments of new genetic screening methods (e.g., microarray-based, comparative genomic hybridization assay (a-CGH), whole genome or exome sequencing technics . . . ) have permitted to detect hundreds of genetic risk factors, including common and rare genetic variants, which can increase the likelihood of ASD (Ronemus M. et al; The role of the novo mutations in the genetics of autism spectrum disorders; Nat Rev Genet. 2014 February; 15(2): 133-41). Nevertheless, causal genetic factors can only be identified in 15 to 20% of patients who are screened, thus the vast majority ASD patients are still considered idiopathic.

Many autism susceptibility genes are known to have important roles in brain development, with functions ranging from synaptic transmission to RNA processing and neurogenesis (Gilman SR et al; Rare de novo variants associated with autism implicate a large functional network of genes involved in information and function of synapses; Neuron. 2011 Jun. 9; 70(5):898-907. O'Roak B J. et al; Sporadic autism exomes reveal a highly interconnected protein network of de novo mutations; Nature. 2012 Apr. 4; 485(7397):246- 50. De Rubeis S. et al; Synaptic, transcriptional and chromatin genes disrupted in autism; Nature. 2014 Nov. 13; 515 (7526): 209-15). However, the plethora of genetic targets has highlighted the need for the ASD research community to understand whether genes implicated in ASD may converge on common cellular and developmental processes.

Evidence has recently accumulated to support the theory that the ever-expanding number of ASD susceptibility genes could in fact converge towards a limited number of molecular pathways. This growing assumption offers important translational opportunities as molecular pathways mediating synaptic and circuit formation are also involved in other physiological processes including modulation of the adaptive and innate immune response (Myka L. Estes M L, McAllister A K (2015), Nature Reviews Neuroscience 16, 469-486), cell proliferation, survival and protein synthesis (Subramanian M, Timmerman C K, Schwartz J L, Pham D L and Meffert M K (2015), Front. Neurosci. 9:313. Tang G. et al. (2014), Neuron. 83, 1131-1143).

Attempts have been previously made to stratify ASD patients into smaller, more homogeneous subgroups by utilizing specific genetic signatures (Bernier et al; Disruptive CHD8 mutations define a subtype of autism early in development; Cell 2014 Jul. 17; 158 (2): 263-276.) or behavioral and clinical endophenotypes (Eapen V. and Clarke R. A.; Autism Spectrum Disorders: From genotypes to phenotypes; Front Hum Neurosci. 2014; 8:914). However, these strategies face difficulty encompassing the genetic and phenotypic heterogeneity of ASD, and may not assist in the identification of specific neurobiological pathways underlying disease. Assays on a molecular basis might provide a way to classify ASD patients. However, because of the intrinsic complexity of ASD, its heterogeneity and the complex intertwining of genetic and environmental causal factors, specific biomarkers for ASD which could be used to establish such an assay have yet to be identified. Moreover, because of their specifity, such biomarkers cannot encompass large groups of ASD patients. Such assays could however in the short term come to support the characterization of genotypically, phenotypically or treatment response pre-identified subgroups. There is therefore a need for an efficient and easy method for diagnosing patients with specific subtypes of ASD who could benefit from targeted pharmaceutical intervention addressing the underlying molecular dysfunction of their ASD subgroup.

Objective Problem to be Solved

The problem to be solved is thus the provision of means to efficiently identify subgroups of ASD patients which show a distinct subtype with regard to multiple underlying genetic and/or molecular causes in order to provide adequate pharmacological therapy.

SUMMARY OF THE INVENTION

The present invention solves the problem by providing a method for differentiating between ASD phenotype 1, phenotype 2 and other ASD patients, wherein the method comprises:
administering an Nrf2-activator to a patient,
identifying the ASD patient as an ASD phenotype 1 patient if the subject shows a negative response, as a phenotype 2 patient if he shows a positive response and as another ASD patient if he does not show a positive nor a negative response,
wherein the subject is a patient previously diagnosed with ASD or a subject displaying clinical signs of ASD.

Likewise, the problem is solved by providing a Nrf2-activator for use in differentiating between ASD phenotype 1 and other ASD patients, wherein the Nrf2-activator is administered to a subject, wherein the subject is a patient previously diagnosed with ASD or a subject displaying clinical signs of ASD and wherein a phenotype 1 patient is identified by a negative response, a phenotype 2 patient is identified by a positive response and other ASD patients are identified by the absence of a positive and a negative response.

DETAILED DESCRIPTION OF THE INVENTION

In one aspect, the present invention relates to a method for differentiating between ASD phenotype 1, ASD phenotype 2 and other ASD patients, wherein the method comprises:
administering an Nrf2-activator to an ASD patient,
identifying the ASD patient as an ASD phenotype 1 patient if the subject shows a negative response, as a phenotype 2 patient if he shows a positive response and as another ASD patient if he does not show a positive nor a negative response,
wherein the subject is a patient previously diagnosed with ASD or a subject displaying clinical signs of ASD.

In another aspect, the invention relates to an Nrf2-activator for use in differentiating between ASD phenotype 1, phenotype 2 and other ASD patients, wherein the Nrf2-activator is administered to a subject, wherein the subject is a patient previously diagnosed with ASD or a subject displaying clinical signs of ASD and wherein a phenotype 1 patient is identified by a negative response, a phenotype 2 patient is identified by a positive response and other ASD patients are identified by the absence of a positive and a negative response.

As used herein, the term autism spectrum disorder (ASD) is understood to cover a family of neurodevelopmental disorders characterized by deficits in social communication and interaction and restricted, repetitive patterns of behavior, interests or activities. In the following, the terms "autism spectrum disorder", "autism" and "ASD" are used interchangeably. The term "idiopathic ASD" refers to ASD having a lack of a clear molecular or genetic alteration causing the reported signs and symptoms. The diagnosis of idiopathic ASD is therefore a diagnosis by exclusion, where the main molecular and genetic known causes of autism must be ruled out Herein, the terms "ASD phenotype 1/2" and "phenotype 1/2" are used interchangeably. The term "patient" refers to "ASD patient" and is intended to cover not only humans diagnosed as having ASD, but also humans suspected of having ASD, i.e. subjects presenting behavioral characteristics of ASD and displaying clinical signs of ASD but who have not yet received a formal validation of their diagnostic.

The person skilled in the art is well aware of how a patient may be diagnosed with ASD. For example, the skilled person may follow the criteria set up in "American Psychiatric Association; Diagnostic and Statistical Manual of Mental Disorders (DSM-5) Fifth edition" to give a subject a diagnosis of ASD. Likewise, ASD patients may have been diagnosed according to standardized assessments tools including but not limited to DSM IV, ICD-9, ICD-10, DISCO, ADI-R, ADOS, CHAT.

In other cases, patients may have a well-established DSM-IV diagnosis of autistic disorder, Asperger's disorder, or pervasive developmental disorder not otherwise specified (PDD-NOS). Additionally, the present invention may be useful for subjects displaying clinical signs of ASD, i.e. persistent deficits in social communication and social interaction across multiple contexts as manifested by the following, currently or by history; restricted, repetitive patterns of behavior, interests, or activities, as manifested by at least two of the following, currently or by history; symptoms present in the early development period (but may not become fully manifest until social demands exceed limited capacities, or maybe masked by learned strategies in later life); symptoms cause clinically significant impairment in social, occupational, or other important areas of current functioning; these disturbances are not better explained by intellectual disability (intellectual development disorder) or global development delay.

ASD may occur with or without accompanying intellectual and/or language impairment. It may be associated with a known medical or genetic condition or an environmental factor or other neurodevelopmental, mental or behavioral disorders.

ASD may occur in different severity levels which may be classified according to impairment in social communication and in terms of restricted, repetitive behavior. Importantly, the term ASD phenotype 1 is not associated with a particular severity level of ASD. The present invention may be applied to patients suffering from any severity level of ASD.

Without being bound by a mechanism, it is believed that ASD patients can be characterized depending on whether or not they show an upregulation, a downregulation or normal levels of expression of biomolecular pathways involved in stress response. Depending on whether and how the level of expression of these pathways in the respective individuals are modified, challenging ASD patients with Nrf2-activators which are known to upregulate the respective pathways will improve or worsen ASD symptoms.

Nrf2-activators are herein defined as any substance that upregulates the expression of the transcription factor Nrf2, also known as Nuclear factor (erythroid-derived 2)-like 2 (NFE2L2) which is, in humans, encoded by the NFE2L2 gene. At the same time, the term "Nrf2-activators" also includes substances that inhibit degradation of Nrf2 or otherwise enhance the activity of Nrf2.

The person skilled in the art is well aware of various substance classes that may be used as Nrf2-activators. These include but are not limited to substances which increases reactive oxygen species (ROS) levels; molecules which directly bind Keap1 or Nrf2, thereby disrupting the interaction between Nrf2 and Keap1 and thus inducing nuclear accumulation and activation of Nrf2; glutathione peroxidase-1 mimetics; seleno-organic antioxidants; molecules increasing expression of anti-oxidant genes through regulating the binding of ARE and Nrf2; molecules enhancing Nrf2 nuclear translocation and activating Nrf2-dependent antioxidant response to overcome stress (e.g., cinnamic aldehyde); molecules reducing the ROS level through activation of Nrf2 and induction of downstream phase II enzyme (e.g., flavonoids); molecules stabilizing Nrf2 and inducing Nrf2 activation through mitochondrial oxidative stress induction (e.g., tertiary butylhydroquinone).

In one embodiment, the Nrf2-activator is selected from the group consisting of isothiocianates (e.g., sulforaphane); polyphenolic molecules (e.g., curcumin); polyphenolic phytoalexins, in particular derivates of stilbene (e.g., resveratrol); α-methyl cinnamic aldehyde; flavonoids (e.g., aspigen, luteolin); pyrazines (e.g., oltipraz); butylated hydroxyanisole, specifically tertiary butylhydroquinone; dimethyl fumarate; monomethyl fumarate; glutathione; benzoselenazoles (e.g., ebselen).

In a preferred embodiment, the Nrf2-activator may be sulforaphane. Preferably, sulforaphane for use according to the present invention is administered at a dosage level of at least 2 μmol/kg for at least 1 day. In a preferred embodiment, sulforaphane is administered at a dosage level between 2 μmol/kg and 5 μmol/kg, preferably 4 μmol/kg per day.

Sulforaphane (1-isothiocyanato-4R-(methylsulfinyl)butane) is an isothiocyanate derived from broccoli. Its therapeutic potential is based on its potent activity in transcriptionally upregulating genes that control mechanisms whereby aerobic cells protect themselves against oxidative stress, inflammation, DNA-damaging electrophiles, and radiation. Sulforaphane may be extracted from plants such as broccoli sprouts, but may also be produced by chemical synthesis. Sulforaphane is a dietary phytochemical, derived from its precursor glucosinolate glucoraphanin, which is widely consumed in cruciferous plant-rich diets. Thus, sulforaphane qualifies for consideration as a food, a dietary supplement, or a drug. Sulforaphane is considered to be of low toxicity, and its administration to humans is well tolerated (Singh K et al., PNAS October, 2014; 111(43); 15550-15555).

As an example, sulforaphane has been suggested as a treatment for ASD (WO 2013/067040). However, the present inventors have surprisingly found that sulforaphane is not effective in reducing disease severity as measured through the ADI-R, SRS and GGI-S/CGI-I in a selected patient cohort, indicating differences in underlying genetic alterations and related metabolomics profile. Thus, the inventors developed the present identification test based on challenging patients by administration of Nrf2-activators in order to identify subsets of patients with common genetic alterations allowing for therapy stratification and optimization.

In another embodiment, the Nrf2-activator may be a sulforaphane analogue. These include 6-isothiocyanato-2-hexanone, exo-2-acetyl-6-isothiocyanatonorbornane, exo-2-isothiocyanato-6-methylsulfonylnorbornane, 6-isothiocyanato-2-hexanol, 1-isothiocyanato-4-dimethylphosphonylbutane, exo-2-(I'hydroxyethyl)-5-isothiocyanatonorbornane, exo-2-acetyl-5-isothiocyanatonorbornane, 1-isothiocyanato-5- methylsulfonylpentane, cis-3-(methylsulfonyl)-cyclohexylmethylisothiocyanante and trans-3- (methylsulfonyl)cyclohexyl-methylisothiocyanante.

In yet another embodiment, the Nrf2-activator may be any selected from sulforaphane, isothiocyanic acid, bardoxolone methyl and fumaric acid esters, 5-(2,2-diferuloylethen-1-yl) thalidomide, ferulic acid, resveratrol, (+)-alpha-viniferin, pallidol, ampelopsin B, quadrangularin A, aspigen, luteolin, 6-C-alpha-L-arabinopyranosyl-8-C-beta-D-glucosylluteolin, 6-hydroxyluteolin 7-O-laminaribioside, 6-hydroxyluteolin, lucenin-2, luteolin 7-O-beta-Dglucoside, luteolin 7-O-neohesperidoside, luteolin-7-O-alpha-L-rhamnoside, isoorientin, carlinoside, 7-O-[beta-D-arabinopyranosyl-(1→6)-beta-D-g lucosyl]luteolin, luteolin Oglucuronoside, orientin, 4',5,7-trihydroxy-3'-methoxyflavone, 5,3'-di-O-methylluteolin, 6-C-[2'-O-alpha-L-rhamnopyranosyl-(1 "→2')]-alpha-L-arabinopyranosyl luteolin, hypolaetin, luteolin 6-C-[beta-D-glucosyl-(1→2)-alpha-L-arabinoside], cassiaoccidentalin B, 6-methoxyluteolin 7-alpha-L-rhamnoside, luteolin 7-O-(6-O-malonyl-beta-D-glucoside), diosmetin, luteolin-4'-O-beta-D-glucopyranoside, 6-C-[2-O-alpha-L-rhamnopyranosyl-(1"→2')]-beta-D-xylopyranosylluteolin, maysin, oltipraz, dimethyl fumarate, fumaric acid, monomethyl fumarate, glutathione, S-sulfanylglutathione, S-(2,4-dinitrophenyl)glutathione, S-(2-hydroxyethyl)glutathione, phytochelatin, eoxin C4, S-acylglutathione, glutathione derivative, ebselen, α-methyl cinnamic aldehyde and 2-tert-butylhydroquinone.

The Nrf2-activator can be used alone or in combination with other compounds. According to the present invention, ASD phenotype 1 patients are identified and characterized by a negative response to administration of an Nrf2-activator.

A negative response may comprise worsening of ASD core and ancillary symptoms. ASD core symptoms include but are not limited to social-interaction difficulties, communication challenges and a tendency to engage in repetitive behavior. ASD ancillary symptoms include but are not limited to intellectual disability, learning disability, genitourinary organ dysfunction (i.e. impairment to initiate urinating), episodes of diarrhea.

A negative or positive response may be transient.

A negative response may also comprise increase in non-compliance/disruptive behaviors, repetitive behaviors and restricted interests (as measured by the ADI-R, ABC (Aberrant Behavior Checklist)-ABC specific subscales (i.e. ABC-I) as well as worsening of preexisting qualitative and quantitative communication and social deficits as measured by Social Responsiveness Scale (SRS).

Particularly, ASD phenotype 1 patients may display a decrease in social responsiveness characterized by but not limited to increased latency or impossibility to respond or establish eye contact, diminished initiation of speech measured by mean number of verbal initiation within a given time interval in a similar contextual environment. Increased latency to response to verbal initiation, decrease in executive functioning including decreased ability to plan and implement multiple step tasks, decrease in behavioral compliance, increased irritability (i.e. ABC irritability subscale), heightened sensitivity to sensory stimuli, decrease in short term memory retention and marked increase or worsening in intensity of idiosyncratic behaviors and postures. A negative response may also comprise or consist of negative variation in scores in standardized tests such as:

Autism Diagnostic Interview-Revised (ADI-R): is a standardized, semi-structured clinician led parent interview. The ADI-R includes 93 items focusing on Early Development, Language/Communication, Reciprocal Social Interactions, and Restricted, Repetitive Behaviors and Interests. (ADI-R; Rutter et al. 2003). It is divided into four different modules.

Aberrant Behavior Checklist (ABC): is a symptoms rating checklist used to assess and classify problem behaviors of children and adults in a variety of settings. The ABC includes 58 items that resolve into five subscales: (1) irritability, (2) lethargy/social withdrawal, (3) stereotypic behavior, (4) hyperactivity/noncompliance, and (5) inappropriate speech. A negative change signifies improvement and a positive change signifies worsening. The value for determining positive or negative response is the change from baseline to 3-5 days after administration of the Nrf2-activator according to the present invention.

Social Responsiveness Scale (SRS). The 65-item SRS is a standardized measure of the core symptoms of autism. Each item is scored on a 4-point Likert scale. The score of each individual item is summed to create a total raw score. Total scores results are as follows:
  0-62: Within normal limits
  63-79: Mild range of impairment
  80-108: Moderate range of impairment
  109-149: Severe range of impairment The value for determining positive or negative response is the change from baseline to 3-5 days after administration of the Nrf2-activator according to the present invention. The total score ranges from 0-149. A negative change signifies improvement and a positive change signifies worsening.

Clinical Global Impression Severity Scale (CGI-S): The CGI-S is a 7-point scale that requires the clinician to rate the severity of the patient's illness at the time of assessment, relative to the clinician's past experience with patients who have the same diagnosis. Considering total clinical experience, a patient is assessed on severity of mental illness at the time of rating:
  1: normal, not at all ill
  2: borderline mentally ill
  3: mildly ill
  4: moderately ill
  5: markedly ill
  6: severely ill
  7: extremely ill The value for determining positive or negative response is the change from baseline to 3-5 days after administration of the Nrf2-activator according to the present invention. The total score ranges from 1-7. A negative change signifies improvement and a positive change signifies worsening.

Clinical Global Impression Improvement Scale (CGI-I): The CGI-I is a 7-point scale measure of overall change of Parent Target Problems (the child's two most pressing problems at screening, as reported by parents), using scores from the Clinical Global Impressions-Severity scale (CGI-S). Scores range from:
  1: very much improved.
  2: much improved.
  3: minimally improved.
  4: no change.
  5: minimally worse.
  6: much worse.
  7: very much worse.

The value for determining positive or negative response is the change from baseline to 3-5 days after administration of the Nrf2-activator according to the present invention. The total score ranges from 1-7. A negative change signifies improvement and a positive change signifies worsening.

Autism Diagnostic Observation Schedule (ADOS): The ADOS is a semi-structured standardized assessment of communication and social interaction that is considered a gold-standard assessment of autism spectrum disorders. It is administered to diagnose autism and determine the level of severity of ASD in patients by evaluating impairments in two specific domains (the Social affect domain and the Restricted and Repetitive 25 behaviors domain). Different modules are used according to age and characteristics of the patients:
  Module 1: children who use little or no phrase speech.
  Module 2: subjects who use phrase speech but do not speak fluently.
  Module 3: younger subjects who are verbally fluent.
  Module 4: adolescent and adults who are verbally fluent. and involve expert clinical judgement of the qualities and behaviors that are at the core of the social/communicative deficits. A negative change signifies improvement and a positive change signifies worsening. The ADOS scoring algorithm consists in 2 raw domain scores that are calibrated on a single 10-point scale, the ADOS-CSS (Calibrated Severity Scores).

Individuals with Scores between 6-10 on ADOS-CSS receive the classification "Autism", those with a CSS of 4-5 "ASD" down to "Nonspectrum" for individuals with CSS of 1-3. The value for determining positive or negative response is the change from baseline to 3-5 days after administration of the Nrf2-activator according to the present invention.

Childhood Autism rating Scales (CARS), (CARS; Schopler et al. 1980, 1988). The CARS consists of 14 domains assessing behaviors associated with autism, with a 15th domain rating general impressions of autism. Each domain is scored on a scale ranging from one to four; higher scores are associated with a higher level of impairment. Total scores can range from a low of 15 to a high of 60; scores below 30 indicate that the individual is in the non-autistic range, scores between 30 and 36.5 indicate mild to moderate autism, and scores from 37 to 60 indicate severe autism (Schopler et al. 1988).

Other means to measure a change in ASD symptoms include: mean length of utterance (MLU) defined as the number of words or morphemes in each of spontaneous utterances. This measure is one of the most robust indices of young children's language acquisition. MLU is used to diagnose language impairments in young children, often defined as an MLU level one standard deviation or more below the mean for the child's age level. Additionally, intellectual functioning as a core symptom of ASD may be measured via the Vineland Adaptive Behavior Scale II (VABS-II), wherein a raise in scores signifies improvement, i.e. positive response. A negative response may also comprise a negative change in one or more indicators measuring core or ancillary symptoms of ASD including: changes in observer reported or computer monitored eye tracking revealing level of interest in social stimuli versus objects, engagement in and responsiveness to social interaction, verbal and nonverbal communication abilities, occurrence of repetitive behaviors, level of intellectual functioning, measurement of attention, quality of motor coordination, quality of sleep, and intensity of symptoms of medical comorbidities (e.g. gastro-intestinal symptoms).

For example, a negative response as defined herein may be identified by a reversible increase of at least 10%, 20%, 30%, 40%, 50%, 60%, 70%, 80%, or 90% in any of ADI-R ABC, ABC-I, SRS, CARS or ADOS scores. In a preferred embodiment, the negative response comprises an increase of at least 10% in total scores in these scales or any increase corresponding to a "minimally worse" (5) and preferably "much worse" (6) or "very much worse" (7) rating on the CGI-I scale.

According to the present invention, ASD phenotype 2 patients are identified and characterized by a positive response to administration of an Nrf2-activator.

A positive response may comprise improvement of autism core and ancillary symptoms, in particular decrease in non-compliance/disruptive behaviors, repetitive behaviors and restricted interests (as measured by the ABC (Aberrant Behavior Checklist-subscales) as well as improvement of pre-existing qualitative and quantitative communication and social deficits as measured by Social Responsiveness Scale (SRS). For example, ASD phenotype 2 patients may display an improvement in social responsiveness characterized by but not limited to decreased latency to respond or establish eye contact, heightened initiation of speech measured by mean number of verbal initiation within a given time interval in a similar contextual environment, decreased latency to respond to verbal initiation, increase in executive functioning including increased ability to plan and implement multiple step tasks, increase in behavioral compliance, decreased irritability (ABC irritability subscale), diminished sensitivity to sensory stimuli, increase in short memory retention and marked decrease or improvement in intensity of idiosyncratic behaviors and postures.

Likewise, a positive response may comprise lowering of absolute scores in standardized tests such as the ADI-R, ABC, ABC-I, SRS, CARS or ADOS or at least a "minimally improved" and preferably a "much improved" or "very much improved" rating on the CGI-I scale.

For example, a positive response may be identified by a reversible decrease of at least 10%, 20%, 30%, 40%, 50%, 60%, 70%, 80%, or 90% in any of ABC-I, SRS, or ADI-R score. In a preferred embodiment, the positive response comprises a decrease of at least 10%.

All effects are reversed promptly (i.e., within 24h to 10 days) after cessation of Nrf2- activator administration.

According to the present invention, a third group of patients are identified and characterized by the absence of a positive and a negative response. Accordingly, these patients show neither a negative response nor a positive response as described above.

In addition to the tests and parameters mentioned above, the skilled person is well aware of other tests and methods to identify a positive or negative response to a particular treatment in ASD patients.

In one aspect of the invention, the Nrf2-activator may be administered for at least 1 day, at least 2, at least 3, at least 4 or at least 5 days. In a preferred embodiment, the Nrf2-activator may be administered for 1 to 7 days, more preferably for 1 to 5 days and, even more preferably, for 5 days. The Nrf2-activator may also be administered for exactly 1, 2, 3, 4 or 5 days. Administration for a determined number of days is necessary in order to standardize the testing procedure. If administration time is short, patients may not show any response at all although they are actually phenotype 1 or 2 patients. If administration continues for a long period of time, adverse effects for phenotype 1 patients will further increase.

According to the invention, the Nrf2-activator may be used in dosages higher than dietary input in order to induce an effect in the patient quickly. For example, the Nrf2-activator may be administered at a dosage level of at least 2 μmol/kg. Preferably, the Nrf2-activator may be administered at a dosage level of 2 to 5 μmol/kg. Most preferred, the Nrf2-activator may be administered at a dosage level of 4 μmol/kg.

The person skilled in the art is aware of ways and methods to administer the Nrf2-activator. For example, the Nrf2-activator may be administered orally, nasally or parenterally. In a preferred embodiment, the Nrf2-activator may be administered orally.

In order to achieve the desired dosage level, the Nrf2-activator may be administered once daily or in several doses per day. In a preferred embodiment, the Nrf2-activator is administered 3 times daily. In another embodiment, the Nrf2-activator is administered 2 times daily. In another embodiment, the Nrf2-activator is administered 1 time per day.

EXAMPLES

Example 1

Materials & Methods

All patients had previously received a diagnosis of ASD according to DSM-IV or DSM-5 criteria supported by either ADI-R or ADOS-2 scores. No exclusion criteria were considered for age, gender, or ethnicity, although only cases presenting with non-syndromic or isolated ASD were included in the study in order to avoid confounding factors.

Individuals with idiopathic ASD were classified as Phenotype 1 is they showed:

at least 1 mandatory criterion:
   enlarged head size versus control population characterized by at least one standard deviations above the mean head circumference (HC) during the first 24 months of life and/or formal macrocephaly (HC>97% of the general population)
   and/or
   cyclical aggravation of core autism symptoms potentiated by periods of infectious events, deciduous tooth loss, post-traumatic injury, endogenous and exogenous temperature variation and at least 2, and most preferably at least 3 out of the following 20 characteristics:
- accelerated hair and nail growth versus control population
- increased tendency to present with lighter colors of skin and eyes as compared to individuals of the same ethnicity
- substantially longer eyelashes than control subjects of the same ethnicity
- at least 5 non-contiguous areas of hypopigmented skin, particularly presenting on the back of the patient
- signs of edema during periods of infectious events, deciduous tooth loss, post-traumatic injury, or endogenous and exogenous factors modifying body temperature; more specifically, facial edema located in the periorbital and forehead areas
- increased blood levels of gamma-glutamyl transpeptidase (GGT) as compared to typically developing individuals of the same age and ethnicity
- Congenital genitourinary malformations and/or functional impairment to initiate urinating
- hypoplasia of the patella
- frequent episodes of diarrhea specifically before the age of 5 years
- frequent episodes of tinnitus
- thinning or absence of the corpus callosum
- positive family history for hematological malignancies in particular but not limited to myeloma and acute promyelocytic leukemia
- positive family history for rheumatoid arthritis, that is at least two affected first-degree relatives in two consecutive generations
- adverse events in response to acetyl-salicylic acid or its derivatives
- iris coloboma, either monolateral or bilateral
- sleep hyperhidrosis particularly as babies, toddlers and young children (notably increased night sweating during infancy and childhood—often reported by relatives to requires bed linen changes
- increased Th1/Th2 ratio (i.e. elevated levels of Interleukin 1 beta, Interleukin 6, TNF-alpha, Interferon gamma)
- congenital accessory or duplicated spleen
- congenital absence of the cisterna chyli
- reported history of mother suffering from viral or bacterial infection during pregnancy and/or biologically confirmed Maternal immune activation during pregnancy Results A cohort of 313 patients with ASD with complete clinical data in the Greenwood Genetic Center (GGC, SC, USA) database was considered.

Out of these 313 patients with ASD in the GGC database, 90 (28.8%) had at least two well documented measures of head circumference taken in the first 24 months of life by a trained physician. Among these 90 patients, 47 (52.2%) matched with at least 1 primary criterion (i.e. head circumference).

The families of the 47 patients with at HC>75 were contacted by telephone to inquire about the presence of the second mandatory criteria for ASD Phenotype 1. The GGC failed to establish contact with the families of 5 of the 47 patients (10.6%). Of the remaining 42 patients from which it was possible to collect further clinical information, 21 (50%) satisfied the ASD Phenotype criteria. Overall, with the exclusion of the 5 cases which could not be followed-up, 21 out of 85 patients (24.7%) fit the criteria for ASD phenotype 1 and showed between 3 and 8 of the secondary characteristics.

Example 2

Materials & Methods

Fifteen of the 21 ASD phenotype 1 patients identified in example 1 were considered for in-vitro analysis. Twenty ASD patients were selected as non-phenotype 1 if they did not match the criteria cited in example 1. Twenty controls were identified as individuals in which no signs or symptoms of neurobehavioral disorders have been detected and were therefore considered as typically developing individuals (TDs).

The phenotype 1 cohort (Ph1) selected for in vitro experiments was composed by 14 males and 1 female (ratio 14:1), with an age range of 2-17 years (average 7.7). For comparison, the non-phenotype 1 (non-ph1) cohort was composed by 19 males and 1 female (ratio 19:1), with an age range of 2-20 years (average 5.25), while the TD cohort was composed by 15 males and 5 females (3:1 ratio) with the age at the time of sample collection ranging from 3 to 8 years (average 5.1)

From all subjects, blood samples were collected and lymphoblastoid cell lines generated. Briefly, tubes containing anticoagulant citrate dextrose (ACD) were used to collect blood samples via venipuncture, in order to ensure that the blood cells remained metabolically active. The tubes were kept at room temperature and processed within 24 hours.

Cell lines were obtained by immortalization of lymphocytes from blood samples using Epstein-Barr virus. The lymphoblastoid cell lines were harvested in Sigma RPMI-1640 with 75 mL fetal bovine serum from Atlanta Biological (Lawrenceville, Ga., USA) and 5 mL L-Glutamine and 5 mL antibiotic/antimycotic from Sigma-Aldrich (St. Louis, Mo., USA).

Energy production of cells was measured using commercially available Phenotype Mammalian MicroArrays (PM-Ms, Biolog, Hayward, Calif., USA).

The compound in each well was designed to be used by the cells, either as the sole energy source or as the metabolic effector influencing the utilization of an energy source ($\alpha$-D-glucose) added in the cell suspension. The production of NADH per well was monitored using a colorimetric redox dye chemistry (Bochner et al. Assay of the multiple energy-producing pathways of mammalian cells. PLoS One 2011, 6(3):e18147). Before plating, cell viability and number were assessed utilizing a BioRad cell counter and a trypan blue dye. The concentration of live cells required for plating was $4 \times 10^5$ cells/mL, corresponding to 20,000 cells per well in a volume of 50 µL. Only cell lines with viability of 55% or above were utilized for the experiments and, in order to minimize artifacts and biases due to prolonged cell culturing of transformed cells, LCLs were not utilized if they had reached 15 passages. Cells were incubated for 48 h at 37° C. in 5% $CO_2$, using the modified Biolog IF-M1 medium.

The Biolog IF-M1 medium was modified for plates PM-M1 to M4 by adding the following to 100 mL of Biolog IF-M1: 1.1 mL of 100× penicillin/streptomycin solution, 0.16 mL of 200 mM glutamine (final concentration 0.3 mM), and 5.3 mL of Fetal Bovine Serum (FBS, final concentration 5%). For plates PM-M5 to M8, 5.5 mM $\alpha$-D-glucose will be added in place of FBS.

During the 48-hour incubation, the only energy source the cells had was the chemical in the well. After this first incubation, Biolog Redox Dye Mix MB was added (10 μL/well) and the plates were incubated under the same conditions for an additional 24 hours. As the cells metabolized the energy source, tetrazolium dye in the media was reduced, producing a purple color according to the amount of NADH generated.

For the last 24 hours of the experiment, the plates were incubated in the Omnilog system, which collects optical density readings every 15 minutes, generating 96 data-points for each well. The system also elaborated the kinetic curve for the metabolic reaction in each well and extrapolated parameters such as slope, highest point, endpoint, area under the curve (AUC), and lag.

At the end of the 24-hour incubation, the plates were analyzed utilizing a microplate reader with readings at 590 and 750 nm. The first value ($A_{590}$) indicated the highest absorbance peak of the redox dye and the second value ($A_{750}$) gave a measure of the background noise. The relative absorbance ($A_{590-750}$) was calculated per well.

Results

The metabolic findings in Phenotype 1 cells showed a distinctive profile and the molecular abnormalities detected in these samples was consistent with activation of Nrf2 and Nrf2 signaling pathway expected in ASD phenotype 1 and ultimately with the expected abnormalities in phenotype 1.

Clear evidence of increased anti-oxidant activity in phenotype 1 cells is provided in Table 1: whenever the cells were exposed to metabolic effectors promoting high energy production (Area Under the Curve, AUC, on the Y axis of the graphics), non-phenotype 1 and control cells generated high NADH levels, while phenotype 1 cells kept a steady profile in the low range of NADH production.

In order to generate more energy than the baseline levels, human cells need to increase the rate of aerobic metabolism, that occurs mostly in mitochondria and is based on oxidative reactions, which often produce reactive oxygen species (ROS) as by-products. The cellular anti-oxidant activity is increased in phenotype 1 cells because of the constitutive activated Nrf2 signaling pathway. Nrf2 activates a battery of antioxidant and detoxifying genes, such as GST (glutathione-S-transferase), NQO1 (NAD(P)H:quinone oxidoreductase 1), HO-1 (heme oxygenase 1), GCS (glutamate-cysteine ligase catalytic subunit), and of genes encoding free radical scavengers, such as superoxide dismutase 1 (SOD1) and catalase (Dreger et al., Nrf2-dependent upregulation of antioxidative enzymes: a novel pathway for proteasome inhibitor-mediated cardioprotection. Cardiovasc Res, 2009. 83(2): p. 354-61; Higgins et al., Transcription factor Nrf2 mediates an adaptive response to sulforaphane that protects fibroblasts in vitro against the cytotoxic effects of electrophiles, peroxides and redox-cycling agents. Toxicol Appl Pharmacol, 2009. 237(3): p. 267-80; Shin et al. Role of the Nrf2-ARE pathway in liver diseases. Oxid Med Cell Longev, 2013. 2013: p. 763257). Thus, the main impact of the Nrf2 antioxidant activity is on ROS and mitochondrial aerobic metabolism. Nrf2 promotes the inhibition of oxidative reactions, resulting in a decreased energy production by mitochondrial aerobic metabolism, which is reflected in the lower levels of NADH generated by phenotype 1 observed in our metabolic assays.

The PI3K-AKT-mTOR pathway is modulated by the Nrf2 signaling pathway. Figure 1 (for area under the curve values, AUC) and Table 1 (for endpoint absorbance values), show a significantly reduced production of NADH in ASD phenotype 1 cells compared to TDs and non-phenotype 1 cells, when cells were exposed to FGF-1 or hGH, two growth factors that selectively target the PI3K-Akt-mTOR by binding the receptor tyrosine kinase (TRK) expressed in the lymphoblast's membrane. Conversely, no significant differences were detected when the cells were exposed to growth factors that target less specifically the PI3K-AKT-mTOR pathway in LCLs, like insulin-like growth factor 1 (IGF-I) and platelet-derived growth factor AB (PDGF-AB).

Nrf2 exerts a stimulatory effect on NF-κB, inducing a pro-inflammatory profile by enhancing the production of Th1 cytokines. As shown in Figure 1, phenotype 1 cells generate significantly lower levels of NADH than other cells when exposed to Th1 cytokines, such as IL-1β and IL-6, than when exposed to Th2 cytokines, like IL-2 and IL-8. A similar trend was noted in the PM-M8 plate when the cells were exposed to the Th1 cytokines IFN-γ and TNF-α.

All in one those results demonstrate a metabolic profile specific of the ASD phenotype 1 when compared to the ASD non-phenotype 1 patients. This metabolic fingerprint validates the existence of a specific ASD phenotype 1.

TABLE 1

List of some of the wells showing different NADH levels between Phenotype 1 and control samples.

| | substrate | UT Phenotype 1 Patient Average | UT Control Average | P value | Note |
|---|---|---|---|---|---|
| A01 | NegativeControl | 1.2826 | 1.5439 | 0.0210 | UT Control average is higher |
| A02 | NegativeControl | 2.1039 | 2.4861 | 0.0360 | UT Control average is higher |
| A05 | Dextrin | 4.4644 | 6.9303 | 0.0007 | UT Control average is higher |
| A08 | Maltotriose | 4.1511 | 2.9542 | 0.0392 | UT Phenotype Patient average is higher |
| A09 | Maltose | 5.6163 | 3.2355 | 0.0024 | UT Phenotype Patient average is higher |
| A10 | D-Trehalose | 2.6570 | 1.9067 | 0.0277 | UT Phenotype Patient average is higher |
| B01 | D-Glucose-6-Phosphate | 2.1269 | 2.8665 | 0.0085 | UT Control average is higher |
| B02 | D-Glucose-1-Phosphate | 3.7488 | 5.5805 | 0.0002 | UT Control average is higher |
| B04 | D-(+)-Glucose | 11.0869 | 13.7383 | 0.0016 | UT Control average is higher |
| B05 | D-(+)-Glucose | 5.3267 | 6.6308 | 0.0027 | UT Control average is higher |
| B10 | Salicin | 3.1458 | 2.1487 | 0.0157 | UT Phenotype Patient average is higher |
| B12 | N-Acetyl-D-Glucosamine | 1.9120 | 1.4505 | 0.0427 | UT Phenotype Patient average is higher |
| C05 | D-Mannose | 5.5082 | 7.2586 | 0.0003 | UT Control average is higher |
| C10 | Sucrose | 1.4825 | 1.1139 | 0.0302 | UT Phenotype Patient averageis higher |
| C12 | Turanose | 2.3111 | 1.6814 | 0.0210 | UT Phenotype Patient average is higher |
| D01 | D-Tagatose | 0.7848 | 0.9824 | 0.0210 | UT Control average is higher |

TABLE 1-continued

List of some of the wells showing different NADH levels between Phenotype 1 and control samples.

|     | substrate | UT Phenotype 1 Patient Average | UT Control Average | P value | Note |
| --- | --- | --- | --- | --- | --- |
| D06 | D-Fructose-6-Phosphate | 1.9697 | 2.8775 | 0.0000 | UT Control average is higher |
| E01 | MelibionicAcid | 1.4852 | 1.9700 | 0.0007 | UT Control average is higher |
| E03 | D-Galactose | 2.8088 | 3.7983 | 0.0030 | UT Control average is higher |
| E07 | Pectin | 3.1739 | 2.3056 | 0.0105 | UT Phenotype Patient average is higher |
| E09 | Thymidine | 0.9345 | 0.8003 | 0.0253 | UT Phenotype Patient average is higher |
| E10 | Uridine | 1.7966 | 1.3593 | 0.0230 | UT Phenotype Patient average is higher |
| E11 | Adenosine | 2.7165 | 1.8644 | 0.0068 | UT Phenotype Patient average is higher |
| E12 | Inosine | 5.0562 | 3.3001 | 0.0044 | UT Phenotype Patient average is higher |
| H01 | AcetoaceticAcid | 1.2179 | 1.4480 | 0.0230 | UT Control average is higher |
| H03 | a-Keto-ButyricAcid | 0.9645 | 1.2604 | 0.0076 | UT Control average is higher |
| H10 | PropionicAcid | 1.1854 | 0.7299 | 0.0003 | UT Phenotype Patient average is higher |
| H11 | AceticAcid | 1.5351 | 1.2154 | 0.0210 | UT Phenotype Patient average is higher |
| H12 | HexanoicAcid | 1.3682 | 1.1210 | 0.0463 | UT Phenotype Patient average is higher |
| A05 | NegativeControl | 5.3075 | 6.4793 | 0.0277 | UT Control average is higher |
| B01 | Resistin | 4.5123 | 5.6797 | 0.0129 | UT Control average is higher |
| B05 | Resistin | 3.6909 | 4.6657 | 0.0129 | UT Control average is higher |
| C03 | Ghrelin | 4.2361 | 5.0063 | 0.0392 | UT Control average is higher |
| C05 | Ghrelin | 4.7857 | 6.2623 | 0.0061 | UT Control average is higher |
| C06 | Ghrelin | 5.7492 | 7.2315 | 0.0143 | UT Control average is higher |
| D01 | Gastrin | 4.6075 | 5.8109 | 0.0129 | UT Control average is higher |
| D02 | Gastrin | 3.6864 | 4.5578 | 0.0210 | UT Control average is higher |
| D03 | Gastrin | 4.7024 | 5.9872 | 0.0253 | UT Control average is higher |
| D04 | Gastrin | 4.6552 | 5.9454 | 0.0173 | UT Control average is higher |
| D05 | Gastrin | 3.3230 | 4.3135 | 0.0068 | UT Control average is higher |
| E01 | hGH(Somatotropin) | 3.5131 | 4.2845 | 0.0302 | UT Control average is higher |
| E02 | hGH(Somatotropin) | 6.1886 | 7.6730 | 0.0302 | UT Control average is higher |
| E03 | hGH(Somatotropin) | 5.3069 | 7.0433 | 0.0024 | UT Control average is higher |
| E04 | hGH(Somatotropin) | 4.9185 | 6.0531 | 0.0643 | UT Control average is higher |
| E05 | hGH(Somatotropin) | 3.0475 | 3.7897 | 0.0463 | UT Control average is higher |
| E06 | hGH(Somatotropin) | 3.3055 | 4.3524 | 0.0030 | UT Control average is higher |
| E07 | IGF-I | 4.1864 | 4.7777 | 0.1394 | UT Control average is higher |
| E08 | IGF-I | 6.0383 | 6.4857 | 0.3819 | UT Control average is higher |
| E09 | IGF-I | 5.0086 | 5.1495 | 0.6808 | UT Control average is higher |
| E10 | IGF-I | 5.7454 | 5.8106 | 0.8051 | UT Control average is higher |
| E11 | IGF-I | 4.1026 | 4.2450 | 0.7051 | UT Control average is higher |
| E12 | IGF-I | 3.8620 | 3.8312 | 0.9607 | UT Phenotype Patient average is higher |
| F01 | FGF-1(aFGF) | 4.6635 | 5.4833 | 0.0191 | UT Control average is higher |
| F02 | FGF-1(aFGF) | 6.4952 | 7.7893 | 0.0545 | UT Control average is higher |
| F03 | FGF-1(aFGF) | 6.7217 | 8.0864 | 0.0463 | UT Control average is higher |
| F04 | FGF-1(aFGF) | 4.6164 | 5.5960 | 0.0392 | UT Control average is higher |
| F05 | FGF-1(aFGF) | 6.2132 | 7.6145 | 0.0689 | UT Control average is higher |
| F06 | FGF-1(aFGF) | 6.2023 | 7.3791 | 0.0926 | UT Control average is higher |
| F07 | PDGF-AB | 3.4671 | 4.1317 | 0.0392 | UT Control average is higher |
| F08 | PDGF-AB | 5.7351 | 6.6622 | 0.1066 | UT Control average is higher |
| F09 | PDGF-AB | 6.4721 | 7.0717 | 0.3136 | UT Control average is higher |
| F10 | PDGF-AB | 4.7311 | 4.8924 | 0.7051 | UT Control average is higher |
| F11 | PDGF-AB | 5.2203 | 5.4621 | 0.5644 | UT Control average is higher |
| F12 | PDGF-AB | 4.2885 | 4.5090 | 0.6568 | UT Control average is higher |
| G01 | IL-1beta | 3.7944 | 4.6514 | 0.0068 | UT Control average is higher |
| G02 | IL-1beta | 5.7966 | 6.7024 | 0.1905 | UT Control average is higher |
| G03 | IL-1beta | 6.0344 | 7.2291 | 0.1585 | UT Control average is higher |
| G04 | IL-1beta | 5.6973 | 6.8322 | 0.0800 | UT Control average is higher |
| G05 | IL-1beta | 6.4106 | 7.7595 | 0.0926 | UT Control average is higher |
| G06 | IL-1beta | 4.4971 | 5.3874 | 0.1142 | UT Control average is higher |
| G07 | IL-2 | 5.6683 | 6.3875 | 0.1687 | UT Control average is higher |
| G08 | IL-2 | 3.7132 | 4.2621 | 0.1585 | UT Control average is higher |
| G09 | IL-2 | 4.6178 | 5.1066 | 0.2538 | UT Control average is higher |
| G10 | IL-2 | 5.8067 | 6.5109 | 0.1585 | UT Control average is higher |
| G11 | IL-2 | 4.0105 | 4.4238 | 0.1394 | UT Control average is higher |
| G12 | IL-2 | 4.6692 | 4.6766 | 0.8823 | UT Control average is higher |
| H01 | IL-6 | 4.4499 | 5.0238 | 0.1687 | UT Control average is higher |
| H02 | IL-6 | 3.4820 | 4.0160 | 0.1142 | UT Control average is higher |
| H03 | IL-6 | 4.3322 | 5.1575 | 0.1222 | UT Control average is higher |
| H04 | IL-6 | 4.3861 | 5.1877 | 0.1487 | UT Control average is higher |
| H05 | IL-6 | 4.3835 | 5.0178 | 0.3467 | UT Control average is higher |
| H06 | IL-6 | 4.7685 | 5.6056 | 0.1487 | UT Control average is higher |
| H07 | IL-8 | 5.0911 | 5.7886 | 0.2538 | UT Control average is higher |
| H08 | IL-8 | 3.6180 | 4.2129 | 0.0994 | UT Control average is higher |
| H09 | IL-8 | 3.6674 | 3.9547 | 0.3770 | UT Control average is higher |
| H10 | IL-8 | 3.3435 | 3.7976 | 0.1585 | UT Control average is higher |
| H11 | IL-8 | 3.4478 | 3.6975 | 0.4582 | UT Control average is higher |
| H12 | IL-8 | 4.6088 | 4.7185 | 0.6808 | UT Control average is higher |

TABLE 1-continued

List of some of the wells showing different NADH levels between Phenotype 1 and control samples.

| | substrate | UT Phenotype 1 Patient Average | UT Control Average | P value | Note |
|---|---|---|---|---|---|
| G01 | IFN-gamma | 4.0356 | 4.9801 | 0.0173 | UT Control average is higher |
| G02 | IFN-gamma | 4.7917 | 5.4039 | 0.2270 | UT Control average is higher |
| G03 | IFN-gamma | 4.8744 | 5.8787 | 0.1066 | UT Control average is higher |
| G04 | IFN-gamma | 3.5975 | 4.4725 | 0.0253 | UT Control average is higher |
| G05 | IFN-gamma | 5.4186 | 6.3358 | 0.2680 | UT Control average is higher |
| G06 | IFN-gamma | 4.4249 | 5.2327 | 0.1066 | UT Control average is higher |
| G07 | TNF-alpha | 4.9584 | 5.5748 | 0.3136 | UT Control average is higher |
| G08 | TNF-alpha | 5.0666 | 6.0854 | 0.0743 | UT Control average is higher |
| G09 | TNF-alpha | 4.1134 | 4.7635 | 0.1687 | UT Control average is higher |
| G10 | TNF-alpha | 4.8733 | 5.5308 | 0.2979 | UT Control average is higher |
| G11 | TNF-alpha | 3.8775 | 4.2126 | 0.4785 | UT Control average is higher |
| G12 | TNF-alpha | 4.3117 | 4.3135 | 0.8307 | UT Control average is higher |

Example 3

Individuals with idiopathic ASD were classified as phenotype 1 is they showed:
  at least 1 mandatory characteristics:
    enlarged head size versus control population characterized by at least one standard deviations above the mean head circumference (HC) during the first 24 months of life and/or formal macrocephaly (HC>97% of the general population)
    and/or
    cyclical aggravation of core autism symptoms potentiated by periods of infectious events, deciduous tooth loss, post-traumatic injury, endogenous and exogenous temperature variation
  and
  at least 2, and most preferably at least 3 of the following 20 characteristics:
    accelerated hair and nail growth versus control population
    increased tendency to present with lighter colors of skin and eyes as compared to individuals of the same ethnicity
    substantially longer eyelashes than control subjects of the same ethnicity
    at least 5 non-contiguous areas of hypopigmented skin, particularly presenting on the back of the patient
    signs of edema during periods of infectious events, deciduous tooth loss, post-traumatic injury, or endogenous and exogenous factors modifying body temperature; more specifically, facial edema located in the periorbital and forehead areas
    increased blood levels of gamma-glutamyl transpeptidase (GGT) as compared to typically developing individuals of the same age and ethnicity
    congenital genitourinary malformations and/or functional impairment to initiate urinating
    hypoplasia of the patella
    frequent episodes of diarrhea specifically before the age of 5 years
    frequent episodes of tinnitus
    thinning or absence of the corpus callosum
    positive family history for hematological malignancies in particular but not limited to myeloma and acute promyelocytic leukemia
    positive family history for rheumatoid arthritis, that is at least two affected first-degree relatives in two consecutive generations
    adverse events in response to acetyl-salicylic acid or its derivatives
    iris coloboma, either monolateral or bilateral
    sleep hyperhidrosis particularly as babies, toddlers and young children (notably increased night sweating during infancy and childhood—often reported by relatives to requires bed linen changes
    increased Th1/Th2 ratio (i.e. elevated levels of Interleukin 1 beta, Interleukin 6, TNF-alpha, Interferon gamma)
    congenital accessory or duplicated spleen
    congenital absence of the cisterna chyli
    reported history of mother suffering from viral or bacterial infection during pregnancy and/or biologically confirmed Maternal immune activation during pregnancy Individuals with idiopathic ASD were classified as phenotype 2 is they showed:
  at least 1 mandatory characteristics:
    reduced head size versus control population characterized by at least one standard deviations below the mean head circumference (HC) during the first 24 months of life and/or formal microcephaly (HC<25% of the general population).
    and/or
    cyclical improvement of core autism symptoms potentiated by periods of infectious events, deciduous tooth loss, post-traumatic injury, endogenous and exogenous temperature variation—and more specifically reduction in severity of autism symptoms during episodes of fever
  and
  at least 2, and most preferably at least 3 of the following 20 characteristics:
    reduced hair and nail growth rate versus control population
    characteristic hyperchromatic spots on the iris
    supernumerary nipples
    postaxial polydactyly, particularly involving the fingers
    duplicated renal pelvis
    frequent episodes of constipation specifically before the age of 5 resistant to dietary measures
    2nd-3rd toe cutaneous syndactyly
    absent or hypoplastic gallbladder
    cyclical worsening of core autism symptoms potentiated by seasonal allergies
    cervical ribs
    dermatological conditions including but not limited to eczema or psoriasis café-au-lait spots on the abdomen and the back areas
raynaud phenomenon, particularly after adolescence
urinary incontinence during childhood
frequent ear infection
Madelung sign
hypotonia
positive family history for pulmonary emphysema
reduced sudation even after physical effort or in response to heat
diffuse hypertrichosis The effects of sulforaphane containing Broccoli sprout extract was observed and quantified in 7 individuals suffering from ASD and previously classified as either phenotype 1 or phenotype 2 patients.

Procedure

We describe a procedure consisting of an evaluation of patients with ASD prior and after administration of broccoli sprout extract. The extract was prepared from selected broccoli seeds known to have high yield of sulforaphane which were surface-disinfected and grown (sprouted) for 3 days in a commercial sprouting facility under controlled light and moisture conditions. A boiling water extract was prepared, filtered, cooled, and treated with the enzyme myrosinase (from daikon sprouts) to convert precursor glucosinolates to isothiocyanates. Behavioral evaluation of patients was performed prior, during and after administration of sulforaphane-containing broccoli sprout extract. Baseline evaluation of patients was performed using standard clinical endpoints (ADI-R subscales ADI-SI, ADI-C and ADI-RI).

Challenge regimen consisted of the administration of a Broccoli Sprout Extract dose corresponding to a total daily dosage of 4 µmol/kg of sulforaphane, administered in 3 doses over the course of the day.

TABLE 2

Calculation used to determine which quantity of fresh broccoli sprouts should be used to reach a sulforaphane dosage of 4 µmol/kg in patients administered dry broccoli extract

| Patient # | Weight of ASD patient (kg) | Sulforaphane daily dose (µmol/kg) | Total daily sulforaphane dose (µmol) | Estimated quantity of dry broccoli extract needed (g) | Actual quantity of fresh 3-day old broccoli sprouts used (g) |
|---|---|---|---|---|---|
| Patient 1 | 50 | 4 | 200 | 9.6-17.8 | 150 |
| Patient 2 | 55 | 4 | 220 | 10.5-19.6 | 150 |
| Patient 3 | 22 | 4 | 88 | 4.2-7.8 | 50 |
| Patient 4 | 65 | 4 | 260 | 12.5-23.1 | 175 |
| Patient 5 | 25 | 4 | 100 | 4.8-8.9 | 50 |
| Patient 6 | 32 | 4 | 128 | 6.1-11.4 | 75 |
| Patient 7 | 37 | 4 | 148 | 7.1-13.2 | 100 |

Steps of the calculation:
Estimated sulforaphane content in 50 grams of dry broccoli extract: 102 to 186 mg
Resulting quantity of dry broccoli extract to get 1 mg of sulforaphane: 270 to 500 mg
Molecular weight of sulforaphane: 177.29 g/mol
Number of moles per milligram of sulforaphane: 5.64 µmol
Estimated quantity of dry broccoli extract to get 1 µmol of sulforaphane: 48 to 89 mg
Relative weight of dry broccoli extract to fresh 3-day old broccoli sprouts: 10% (90% is water)
Estimated quantity of fresh 3-day old broccoli sprouts to get 1 µmol of sulforaphane: 480 to 890 mg The assessment of baseline scores and post challenge test scores was conducted by two experienced clinicians with extensive experience in conducting ASD clinical assessments, both of which separately rated the patients. In case of diverging scores in test subscales at baseline or after administration of the challenge test, the lowest severity score was retained. Assessment of clinical endpoints was performed at day 3 of administration of challenge test. Behavioral Outcome Measures: (primary efficacy endpoints): ABC, SRS; CGI-S, CGI-I and ADI-R (ADI-SI, ADI-C, ADI-RI).

In order to confirm phenotype 1 patient, at least one of the following primary outcomes had to be attained after challenging the patient by with sulforaphane administration:

ADI-R: at least 10% increase in ADI-R scores, preferably but not limit to the following subscales: ADI-SI, ADI-C.

CGI-I: patient rated as much worse or very much worse.

In order to confirm the phenotype 2, at least one of the following primary outcomes had to be attained after challenging the patient with sulforaphane administration:

ADI-R: at least 10% decreased in ADI-R scores, preferably but not limit to the following subscales: ADI-SI, ADI-C.

CGI-I: patient rated as much improved or very much improved

Results

Demographics: Five male patients, diagnosed by experienced clinical psychiatrist using strict DSM-5 criteria for Autism Spectrum Disorder. Patient 5 had a history of neurological disease and was treated with Lithium (concomitant medication).

All patients were classified as suffering from a non-syndromic type of autism spectrum disorder. None of them was reported to carry any known autistic linked single gene disorder or copy number variation (CNV) or any other structural variants Four patients used functional language, whereas the remaining one did not (Patient 2). Thus, that last subject was solely administered B1 and B4 module of the "Qualitative abnormalities in Communication" domain.

All patients matched the ASD phenotype 1 criteria.

Scores for the ADI-R in all subdomains were above the autism cut off (ADI-R-SI cut off=10, ADI-R C Verbal cut off=8, Nonverbal cut off=7; ADI-R-RI cut off=3) in all subjects validating preexisting clinical diagnosis of ASD. ADI-R baseline evaluations were conducted prior to any change or adjunct in intervention (either pharmaceutical and/or behavioral).

TABLE 3

ASD diagnostic scores prior to challenge test, cut off for ASD specified in brackets).

| Patient | ADI-R-SI | ARI-R-C | ADI-R-RI |
|---|---|---|---|
| Patent 1 | 20 (10) | 10 (7) | 3 (3) |
| Patient 2 | 25 (10) | 12 (8) | 5 (3) |
| Patient 3 | 18 (10) | 15 (8) | 3 (3) |
| Patient 4 | 20 (10) | 14 (8) | 3 (3) |
| Patient 5 | 16 (10) | 12 (8) | 3 (3) |

Summary of the standardized scores showing the effect of Broccoli Sprout Extract (sulforaphane) administration in all five patients:

TABLE 4

ASD scores comparison prior and during challenge test.

| Standardized test | Patient 1 B score | Patient 1 S score | Change (%) |
|---|---|---|---|
| ADI-R-SI | 20 | 24 | 20 |
| ADI-R-C | 10 | 12 | 20 |
| ADI-R-RI | 3 | 4 | 33 |

| Standardized test | Patient 2 B score | Patient 2 S score | Change (%) |
|---|---|---|---|
| ADI-R-SI | 25 | 28 | 11 |
| ADI-R-C | 12 | 16 | 33 |
| ADI-R-RI | 5 | 7 | 40 |

| Standardized test | Patient 4 B score | Patient 4 S score | Change (%) |
|---|---|---|---|
| ADI-R-SI | 20 | 24 | 20 |
| ADI-R-C | 14 | 19 | 36 |
| ADI-R-RI | 3 | 4 | 33 |

| Standardized test | Patient 5 B score | Patient 3 S score | Change (%) |
|---|---|---|---|
| ADI-R-SI | 16 | 21 | 31 |
| ADI-R-C | 12 | 17 | 42 |
| ADI-R-RI | 3 | 4 | 33 |

Note:
B score = Baseline ADI-R scores, S score = ADI-R scores on day 3 of the challenge test administration.

We report a significant worsening of ADI-R subscales ADI-SI, ADI-C and ADI-RI in all 5 patients following broccoli sprout extract (sulforaphane) administration in the context of a challenge test. Experienced clinician and parental/primary caretaker reported observation served to determine CGI-I score after 3 days of broccoli sprout extract (sulforaphane) administration.

TABLE 5

CGI-S and CGI-I values after challenge test

| Patient | GGI-S | CGI-I | Clinical significance |
|---|---|---|---|
| Patient 1 | 5 | 6 | Much worse |
| Patient 2 | 6 | 6 | Much worse |
| Patient 3 | 6 | 7 | Very much worse |
| Patient 4 | 5 | 7 | Very much worse |
| Patient 5 | 4 | 6 | Much worse |

Example 4

Two male patients with mild autism which were classified as phenotype 2 ASD patients and treated as described in example 3

TABLE 6

Experienced clinician and parental/primary caretaker reported observation served to determine CGI-I score after 3 days of sulforaphane administration.

Patient 1

| Standardized test | Patient 1 B score | Patient 1 S score | Change (%) |
|---|---|---|---|
| ADI-R-SI | 16 | 12 | −33 |
| ADI-R-C | 12 | 10 | −20 |
| ADI-R-RI | 3 | 3 | 0 |

TABLE 6-continued

Experienced clinician and parental/primary caretaker reported observation served to determine CGI-I score after 3 days of sulforaphane administration.

Patient 2

| Standardized test | Patient 2 B score | Patient 2 S score | Change (%) |
|---|---|---|---|
| ADI-R-SI | 16 | 14 | −14 |
| ADI-R-C | 11 | 9 | −22 |
| ADI-R-RI | 5 | 4 | −25 |

B = ADI-R scores prior to administration of sulforaphane, S score = ADI-R scores on day 3 of the challenge test administration.

TABLE 7

CGI-S and CGI-I values after challenge test

| Patient | GGI-S | CGI-I | Clinical significance |
|---|---|---|---|
| Patient 1 | 4 | 2 | Very much improved |
| Patient 2 | 4 | 2 | Very much improved |

The invention claimed is:

1. A method for inducing a positive response in an Autism Spectrum Disorders (ASD) phenotype 2 subject, comprising:
    administering from 2 to 5 µmol/kg of a Nrf2-activator to a subject wherein the subject is (ASD) phenotype 2 and has previously been diagnosed with idiopathic ASD or has displayed clinical signs of ASD, wherein a positive response is induced in the subject by the administration of the Nrf2-activator and
    wherein the Nrf2-activator is administered for no longer than 5 days.

2. The method of claim 1, wherein the positive response comprises one or more selected from a decrease in scores of Aberrant Behavior Checklist I (ABC-I), Social Responsiveness Scale (SRS), Clinical Global Impressions-Global Improvement (CGI-I) Ohio Autism Clinical Impression Scale-Improvement (OACSI-I), Clinical Global Impressions-Severity of illness (CGI-S) Ohio Autism Clinical Impression Scale-Severity (OACSI-S) or Autism Diagnostic Observation Schedule (ADOS), decrease latency to respond to eye contact, heightened initiation of speech measured by mean number of verbal initiation within a given time interval in a similar contextual environment, decreased latency to response to verbal initiation, increase in executive functioning, increased ability to plan and implement multiple step tasks, increase in behavioral compliance, decreased irritability, diminished sensitivity to sensory stimuli, increase in short term memory retention and marked decrease of idiosyncratic behaviors and postures.

3. The method of claim 1, wherein the Nrf2-activator is selected from the group consisting of sulforaphane, curcumin, resveratrol, aspigen, luteolin, oltipraz, dimethyl fumarate, monomethyl fumarate, glutathione, ebselen, α-methyl cinnamic aldehyde, and 2-tertbutylhydroquinone.

4. A method for inducing a positive response in an autism spectrum disorder (ASD) phenotype 2 subject, comprising:
    administering a Nrf2-activator to a subject for a duration of no longer than 5 days, wherein the subject (ASD) phenotype 2 and has previously been diagnosed with idiopathic ASD or has displayed clinical signs of ASD, and wherein a positive response is induced in the subject by the administration of the Nrf2-activator.

* * * * *